US012761183B2

(12) United States Patent
Yang et al.

(10) Patent No.: US 12,761,183 B2
(45) Date of Patent: Oct. 13, 2026

(54) MICROBIAL CONCENTRATION DETECTION ELEMENT IN UNKNOWN SOLUTION

(71) Applicant: GIST(Gwangju Institute of Science and Technology), Gwangju (KR)

(72) Inventors: Sung Yang, Gwangju (KR); Ye Sung Lee, Gwangju (KR); Soo Sung Kim, Gwangju (KR)

(73) Assignee: GIST(Gwangju Institute of Science and Technology), Gwangju (KR)

( * ) Notice: Subject to any disclaimer, the term of this patent is extended or adjusted under 35 U.S.C. 154(b) by 251 days.

(21) Appl. No.: 18/781,874

(22) Filed: Jul. 23, 2024

(65) Prior Publication Data

US 2024/0377356 A1 Nov. 14, 2024

Related U.S. Application Data

(63) Continuation of application No. PCT/KR2023/001088, filed on Jan. 25, 2023.

(30) Foreign Application Priority Data

Jan. 25, 2022 (KR) ........................ 10-2022-0010371
Mar. 31, 2022 (KR) ........................ 10-2022-0040716

(51) Int. Cl.
*G01N 27/447* (2006.01)
*C12Q 1/06* (2006.01)
(Continued)

(52) U.S. Cl.
CPC ........... *G01N 27/4473* (2013.01); *C12Q 1/06* (2013.01); *G01N 27/27* (2013.01); *G01N 27/28* (2013.01); *G01N 27/44756* (2013.01)

(58) Field of Classification Search
CPC ......... G01N 27/4473; G01N 27/44713; G01N 27/44717; G01N 27/44769; G01N 27/447;
(Continued)

(56) References Cited

U.S. PATENT DOCUMENTS

2013/0105317 A1* 5/2013 Weber .................... B03C 5/024 204/603
2020/0206740 A1 7/2020 Chiu et al.

FOREIGN PATENT DOCUMENTS

JP 2002-153297 A 5/2002
JP 2003-000224 A 1/2003
(Continued)

OTHER PUBLICATIONS

Cetin et al. Biomicrofluidics, 10, 2016 (Year: 2016).*
International Search Report issued in PCT/KR2023/001088; mailed May 9, 2023.

*Primary Examiner* — Gurpreet Kaur
(74) *Attorney, Agent, or Firm* — Studebaker Brackett PLLC

(57) ABSTRACT

The present disclosure relates to a microbial concentration detection element in an unknown solution. In more detail, the microbial concentration detection element includes: a preprocessing unit configured to produce a microbe substitution solution by transferring microbes in an unknown solution containing detection target microbes into a reference solution through acoustophoresis, and to calculate electrical property information of the microbe substitution solution; and a microbe concentration measurement unit configured to separate the microbe substitution solution into a microbe concentration solution and a filtered solution through dielectrophoresis on the basis of the electrical
(Continued)

property information measured by the preprocessing unit, and then measure a microbial concentration of the microbe concentration solution.

12 Claims, 8 Drawing Sheets

(51) Int. Cl.
*G01N 27/27* (2006.01)
*G01N 27/28* (2006.01)

(58) Field of Classification Search
CPC .. G01N 27/27; G01N 27/28; G01N 27/44756; G01N 33/569; G01N 33/56911; G01N 33/487; G01N 15/0606; G01N 15/0656; G01N 15/01; C12Q 1/04; C12Q 1/06; B03C 5/005
See application file for complete search history.

(56) References Cited

FOREIGN PATENT DOCUMENTS

| | | | |
|---|---|---|---|
| JP | 2010-252785 | A | 11/2010 |
| KR | 10-2012-0066100 | A | 6/2012 |

* cited by examiner

MICROBIAL CONCENTRATION DETECTION ELEMENT IN UNKNOWN SOLUTION

CROSS REFERENCE TO RELATED APPLICATION

The present application is a continuation of International Patent Application No. PCT/KR2023/001088, filed on Jan. 25, 2023, which claims priority to Korean Patent Applications Nos. 10-2022-0010371, filed Jan. 25, 2022 and 10-2022-0040716, filed Mar. 31, 2022, the entire contents of which are incorporated herein for all purposes by this reference.

TECHNICAL FIELD

The present disclosure relates to a microbial concentration detection element in an unknown solution and, in more detail, a microbial concentration detection element in an unknown solution that detects microbial concentration using positive dielectrophoresis force in a preprocessed unknown solution.

BACKGROUND ART

Dielectrophoresis was defined by Pohl in 1951. Dielectrophoresis means a phenomenon that when a particle is placed in a non-uniform electric field, directional force is applied to the particle due to a dipole induced at the particle. The magnitude of force depends on the electrical property and the dielectric property of a particle and a medium, the frequency of an AC electric field, etc., and it is possible to control movement of a particle using this characteristic. The dielectrophoresis technology can be applied to all of particles that can be polarized, so it can be used to move, separate, capture, etc. various organic particles including a cell.

The procedures that are used to detect microbes in the related art are typically accompanied with a step of culturing a specimen. In this case, a target microbe may be cultured in a culture medium that is specific to the target microbe. Such a culture method that is the most generally used is required to culture a microbe over 24 hours, so it has a problem of taking to much time.

Further, immunochromatography and RT-PCR also have problems that it takes a long time to detect, it is difficult to achieve accurate detection when a small amount of sample is used and the microbial concentration is low, there is a high possibility of showing a wrong result.

Accordingly, a preprocessing process for increasing microbial concentration is required for accurate detection. However, there is a problem that sensors integrated with a concentrating function are very limited and existing integrated sensors have a very low processing speed, studies on this problem is not quite sufficient.

DISCLOSURE

Technical Problem

An objective of the present disclosure is to provide a microbial concentration detection element in an unknown solution using dielectrophoresis force.

Another objective of the present disclosure is to provide a microbial concentration detection element in an unknown solution in which dielectrophoresis force is smoothly applied to microbes.

Technical Solution

A microbial concentration detection element in an unknown solution according to an embodiment of the present disclosure includes: a preprocessing unit configured to produce a microbe substitution solution by transferring microbes in an unknown solution containing detection target microbes into a reference solution through acoustophoresis, and to calculate electrical property information of the microbe substitution solution; and a microbe concentration measurement unit configured to separate the microbe substitution solution into a microbe concentration solution and a filtered solution through dielectrophoresis on the basis of the electrical property information measured by the preprocessing unit, and then measure a microbial concentration of the microbe concentration solution.

The preprocessing unit includes: an inlet part into which the unknown solution and the reference solution are separated fed; a substitution part configured to produce a microbe substitution solution by transferring microbes contained in the unknown solution fed through the inlet part into the reference solution through acoustophoresis; a first discharge part configured to separately discharge the microbe substitution solution produced at the substitution part and the unknown solution; and an electrical property calculation unit configured to calculates electrical property information of the microbe substitution solution that is discharged through the first discharge part.

The electrical property calculation unit includes: an impedance measuring unit configured to measure impedance of the microbe substitution solution that is discharged through the first discharge part; and a calculator configured to calculate electrical property information on the basis of impedance measured by the impedance measuring unit.

The impedance measuring unit includes: a current measuring unit configured to measure a current that is applied to the microbe substitution solution that is discharged through the first discharge part; and a voltage measuring unit configured to measure a voltage that is applied to the microbe substitution solution that is discharged through the first discharge part.

The electrical property information is electrical conductivity, permittivity, and a Clausius-Mossotti (CM) factor.

The microbe concentration measurement unit includes: a separation part configured to separate the microbe substitution solution into a microbe concentration solution and a filtered solution using positive dielectrophoresis force; a concentration measurement part configured to measure a microbe concentration of the microbe concentration solution separated by the separation part; and a second discharge part configured to separately discharge the microbe concentration solution and the filtered solution separated by the separation part.

The separation part includes: a substitution solution reception part configured to receive the microbe substitution solution; a plurality of herringbone electrode parts installed at the substitution solution reception part, formed in a herringbone pattern shape in which electrodes bend at predetermined angles and extend from bending points, and configured to separate the microbe substitution solution into a microbe concentration solution and a filtered solution as microbes contained in the microbe substitution solution in the substitution solution reception part are moved along the bending points by positive dielectrophoresis force; and a first power application part configured to apply power to the herringbone electrode part on the basis of electrical property information calculated by the electrical property calculation unit so that positive dielectrophoresis force can be generated at the herringbone electrode part.

The herringbone electrode part includes a first electrode section and a second electrode section, the first and second electrode sections are sequentially arranged with a predetermined gap therebetween, the first electrode section is composed of a plurality of first electrodes arranged with predetermined gaps therebetween on the basis of flow of the microbe substitution solution such that the microbes can be induced to the bending points by smoothly applying positive dielectrophoresis force to microbes contained in the microbe substitution solution received in the substitution solution reception part, the second electrode section is composed of a plurality of second electrodes arranged with predetermined gaps therebetween on the basis of flow of the microbe substitution solution passing through the first electrode section such that positive dielectrophoresis force can be smoothly applied, the first electrodes are formed at different angles, and the second electrodes are formed at a uniform angle.

The concentration measurement part includes: a detection electrode part installed in the substitution solution reception part and configured to capture microbes concentrated in a microbe substitution solution using positive dielectrophoresis force; a second power application part configured to apply power to the detection electrode part for a predetermined time so that positive dielectrophoresis force can be generated; and a microbe concentration detection part configured to measure a total microbe concentration by measuring electrical signal variation generated for a predetermined time at the detection electrode part.

The detection electrode part is composed of one or more pairs of IDE electrodes.

The microbial concentration detection element further includes an electrochemical sensor unit configured to measure a concentration of a strain of each of microbes in a microbe concentration solution that is discharged from the microbe concentration measurement unit, and the electrochemical sensor unit includes: a sample solution injection part into which the microbe concentration solution is injected; a reaction solution injection part that is connected with the sample solution injection part and into which reaction solution is injected; a solution reception part that is connected with the sample solution injection part and into which the microbe concentration solution and the reaction solution are sequentially received; an incubation part configured to incubate microbes of the microbe concentration solution received in the solution reception part for a predetermined time; a microbe strain-specific concentration measurement part configured to measure a concentration of a strain of each of microbes incubated in the incubation part; and a solution discharge part connected with the solution reception part and configured to discharge the microbe concentration solution or the reaction solution from the solution reception part.

The microbial concentration detection element includes: a shutoff valve installed at the sample solution injection part and configured to block movement of the microbe concentration solution or the reaction solution; and a controller configured to control the shutoff valve such that a microbe concentration solution and a filtered solution are sequentially received in the solution reception part in order to measure a concentration of a strain of each of microbes incubated in the incubation part.

Advantageous Effects

The microbial concentration detection element in an unknown solution according to an embodiment of the present disclosure has the following effects.

(1) It is possible to separate a microbe substitution solution into microbe concentration solution and a filtered solution through positive dielectrophoresis force by supplying power to the herringbone electrode part on the basis of electrical property information of a preprocessed microbe substitution solution.

(2) The a herringbone electrode part is designed on the basis of flow of a microbe substitution solution flowing into the microbe substitution solution reception part, whereby it is possible to smoothly apply positive dielectrophoresis force to microbes.

MODE FOR INVENTION

Figure 1:
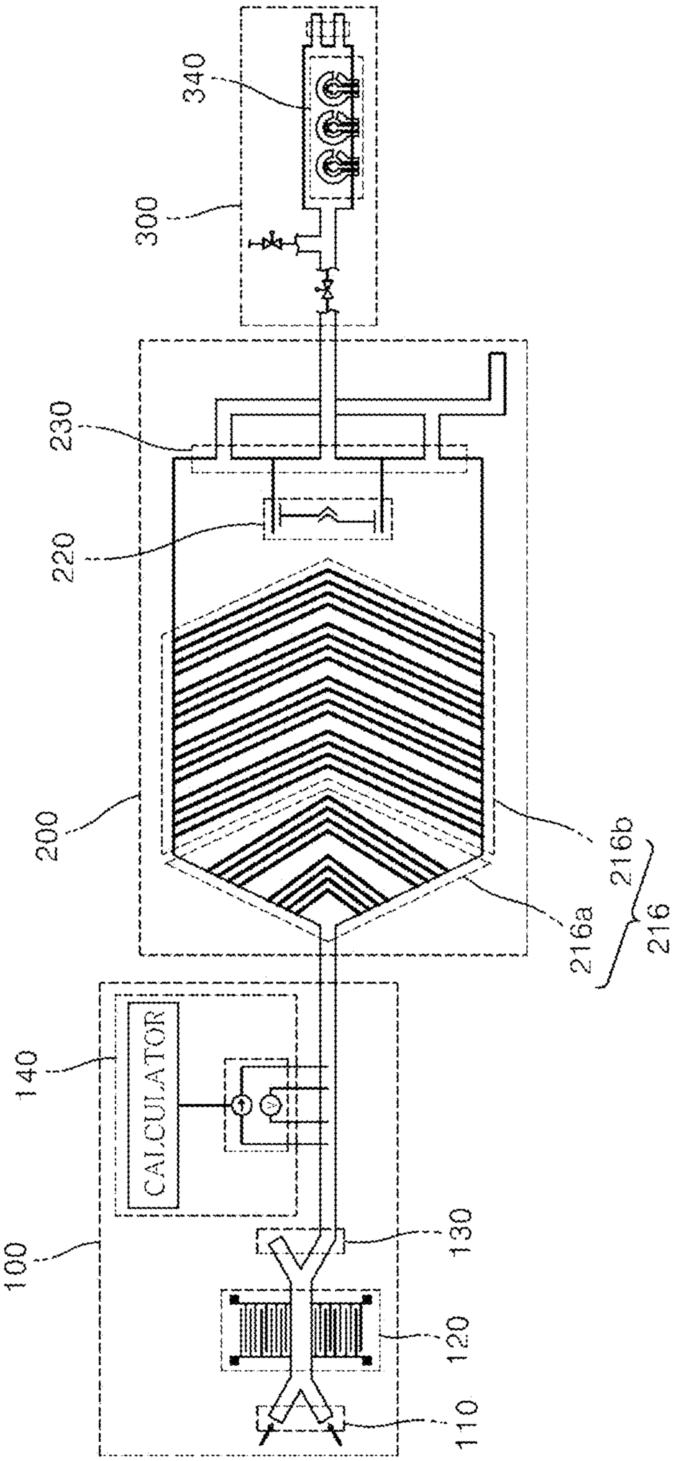
FIG. 1 is a cross-sectional view showing a microbial concentration detection element according to an embodiment of the present disclosure.

Hereafter, a 'microbial concentration detection element in an unknown solution' according to an embodiment of the present disclosure is described in detail with reference to the accompanying drawings. The present disclosure may be modified in various ways and implemented by various exemplary embodiments, so that specific exemplary embodiments are shown in the drawings and will be described in detail herein. However, it is to be understood that the present disclosure is not limited to the specific exemplary embodiments, but includes all modifications, equivalents, and substitutions included in the spirit and the scope of the present disclosure. Similar reference numerals are assigned to similar components in the following description of drawings. In the accompanying drawings, the dimensions of structures were exaggerated larger than the actual dimensions to make the present disclosure clear.

Terms used in the specification, “first”, “second”, etc., may be used to describe various components, but the components are not to be construed as being limited to the terms. The terms are used only to distinguish one component from another component. For example, the “first” component may be named the “second” component, and vice versa, without departing from the scope of the present disclosure.

Terms used in the present specification are used only to describe specific exemplary embodiments rather than limiting the present disclosure. Singular forms are intended to include plural forms unless the context clearly indicates otherwise. It will be further understood that the terms “comprises” or “have” used in this specification specify the presence of stated features, steps, operations, components, parts, or a combination thereof, but do not preclude the presence or addition of one or more other features, numerals, steps, operations, components, parts, or a combination thereof.

Unless defined otherwise, it is to be understood that all the terms used in the specification including technical and scientific terms have the same meaning as those that are understood by those who skilled in the art. It will be further understood that terms defined in dictionaries that are commonly used should be interpreted as having meanings that are consistent with their meanings in the context of the relevant art and will not be interpreted in an idealized or overly formal sense unless expressly so defined herein.

Figure 2:
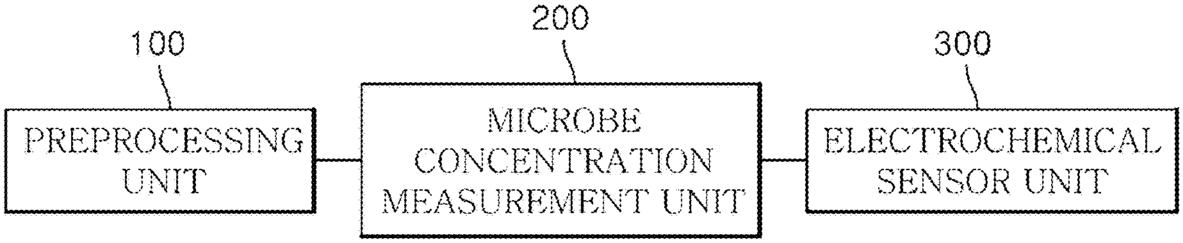
FIG. 2 is a block diagram showing a microbial concentration detection element in an unknown solution according to an embodiment of the present disclosure.

Referring to FIGS. 1 and 2, a microbial concentration detection element 10 in an unknown solution according to an embodiment of the present disclosure includes a preprocessing unit 100, a microbe concentration measurement unit 200, and an electrochemical sensor unit 300.

Figure 3:
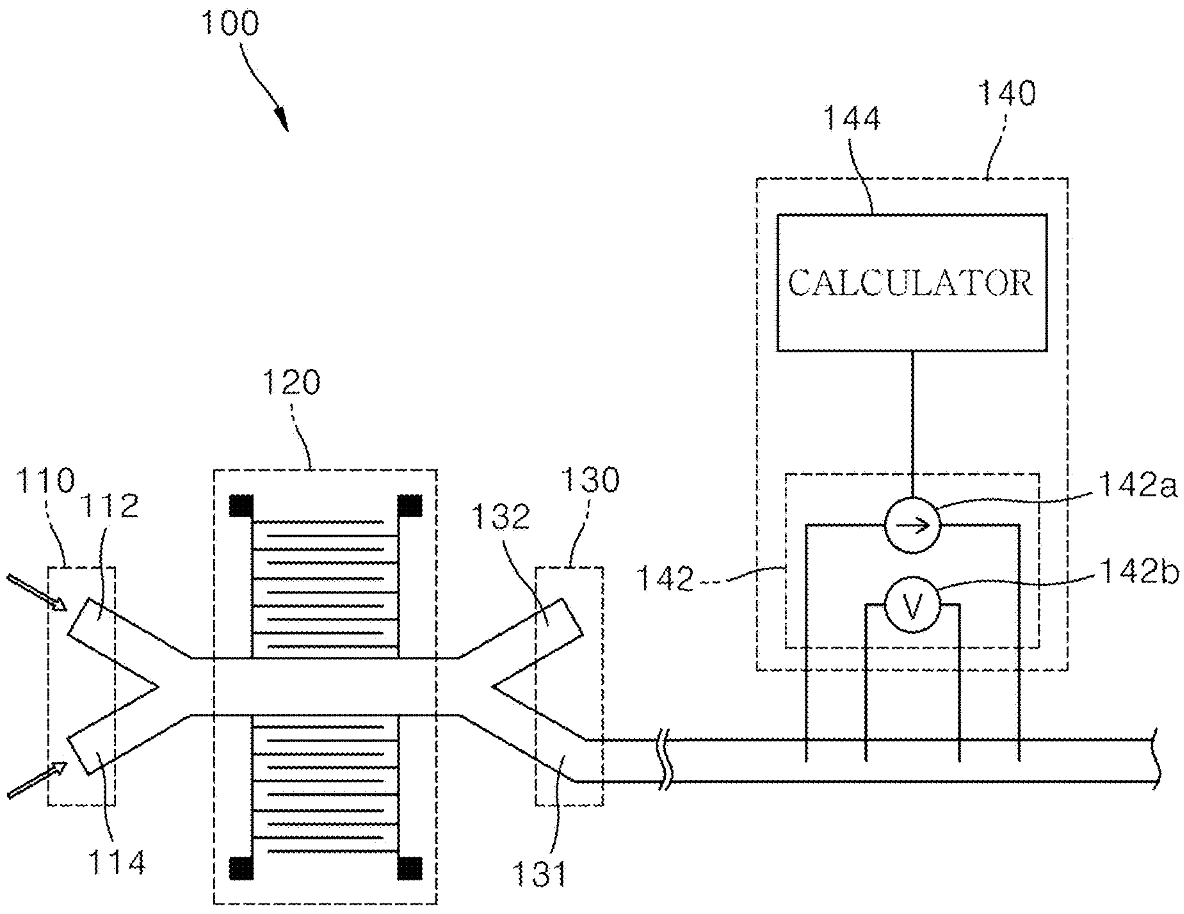
FIG. 3 is a cross-sectional view showing a preprocessing unit of the microbial concentration detection element according to an embodiment of the present disclosure.
Figure 4:
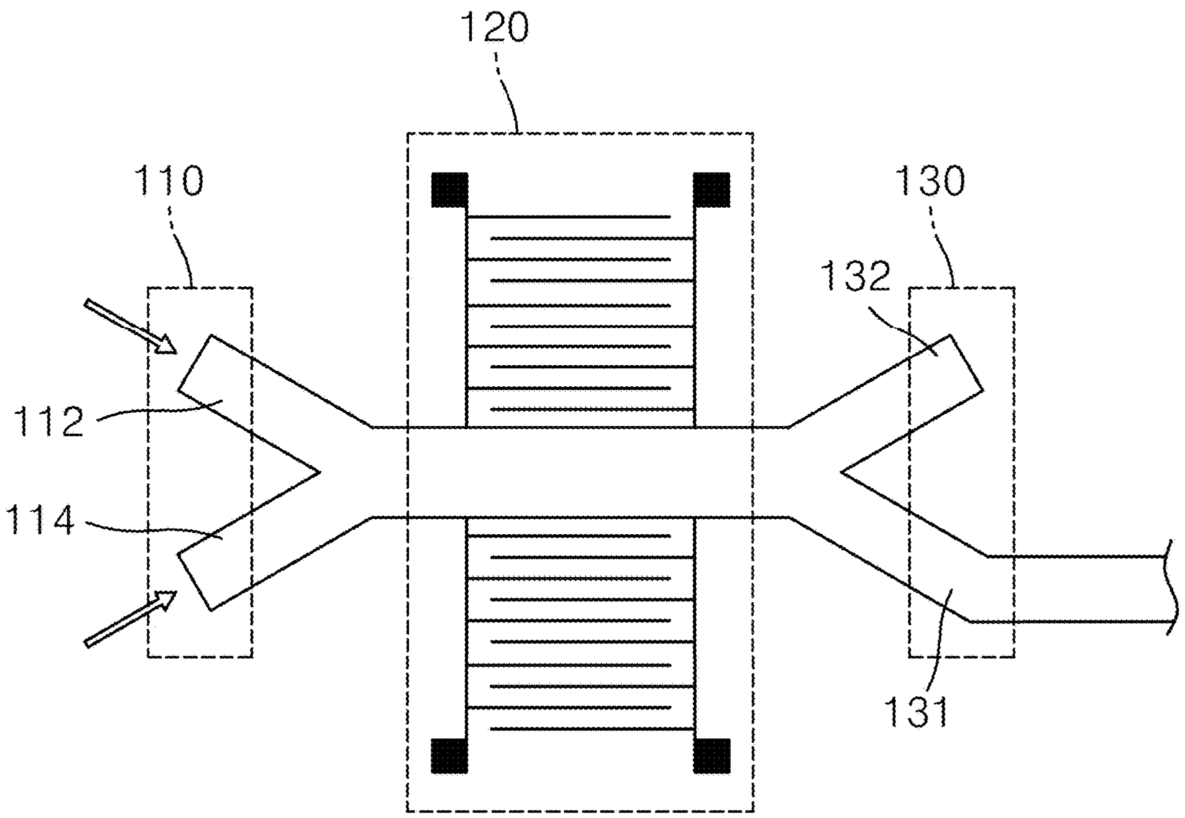
FIG. 4 is a cross-sectional view showing a substitution unit of the microbial concentration detection element according to an embodiment of the present disclosure.
Figure 5:
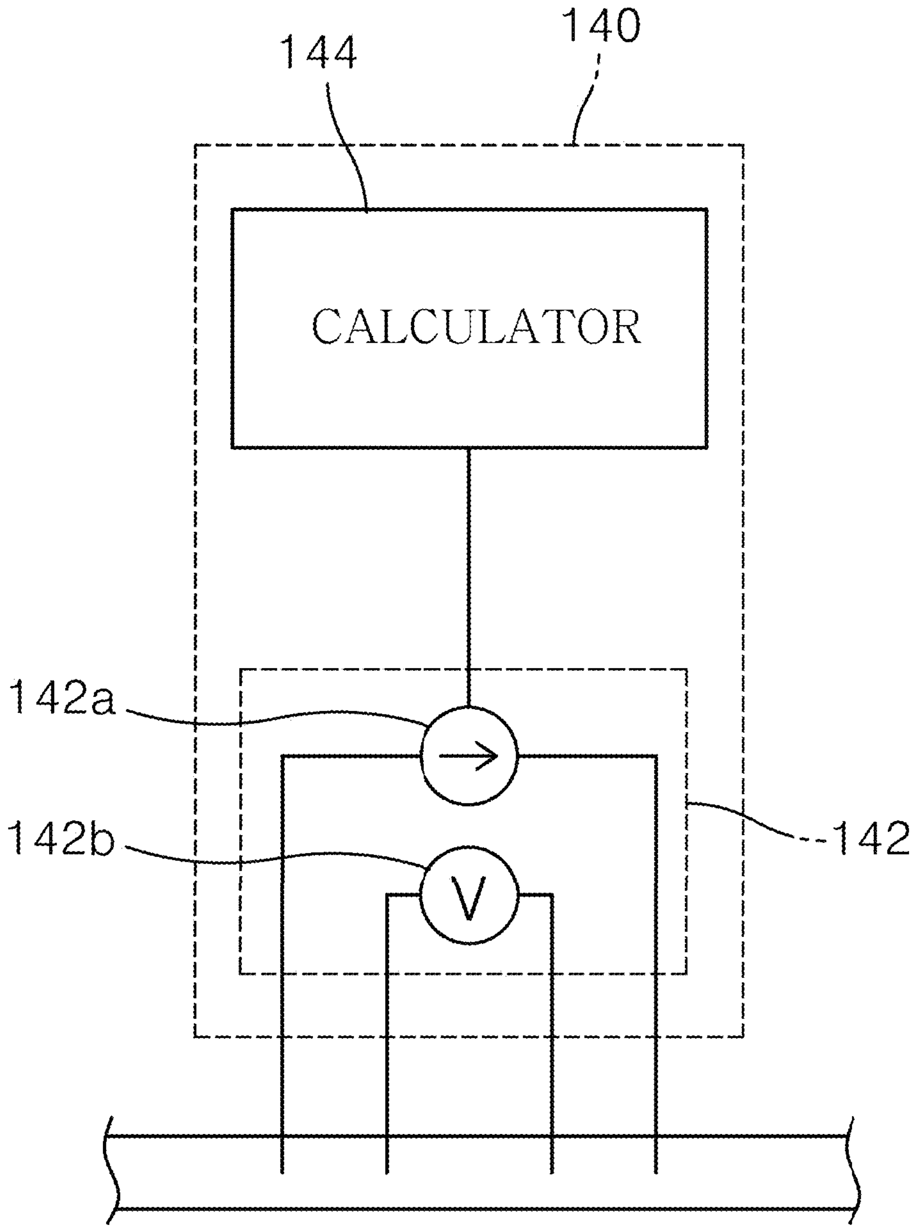
FIG. 5 is a cross-sectional view showing an electrical property calculation unit of the microbial concentration detection element according to an embodiment of the present disclosure.

Referring to FIGS. 3 to 5, the preprocessing unit 100 produces a microbe substitution solution by transferring microbes in an unknown solution containing detection target microbes into a reference solution through acoustophoresis, and calculates electrical property information of the microbe substitution solution.

The preprocessing unit 100 includes an inlet part 110, a substitution part 120, a first discharge part 130, and an electrical property calculation unit 140.

The inlet part 110 includes a first inlet 112 and a second inlet 114. An unknown solution containing detection target microbes is injected into the first inlet 112. A reference solution is injected into the second inlet 114 by the same amount as the unknown solution. The reference solution may be a sheath solution that is used to transfer unknown particles or microbes included in a solvent.

An unknown solution fed through the inlet 112 and a reference solution are injected while maintaining the interface without mixing, and in this process, microbes contained in the unknown solution fed through the inlet part 110 are transferred into the reference solution by acoustophoresis, whereby the substitution unit 120 produced a microbe substitution solution. Since the substitution unit 120 produces a microbe substitution solution, it is possible to exclude the influence of the solvent of an unknown solution when applying positive dielectrophoresis force to be described below to the microbe substitution solution.

The sonic wave that is used for the acoustophoresis may be a surface acoustic wave or a bulk acoustic wave formed in an Interdigitated electrode (IDE) structure.

The first discharge part 130 includes a substitution solution outlet 131 and a residual solution outlet 132.

A microbe substitution solution produced by substitution of an unknown solution containing detection target microbes due to acoustophoresis in the substitution unit 120 is discharged through the substitution solution outlet 131.

A residual solution not containing detection target microbes due to substitution of an unknown solution containing the detection target microbes with a reference solution is discharged through the residual solution outlet 132.

The electrical property calculation unit 140 calculates electrical property information of the microbe substitution solution that is discharged through the first discharge part 130 and checks whether microbes of the unknown solution have been normally transferred to a reference solution. The electrical property information may be electrical conductivity, permittivity, and a Clausius-Mossotti (CM) factor.

The electrical property calculation unit 140 includes an impedance measuring unit 142 and a calculator 144.

The impedance measuring unit 142 measures the impedance of a microbe substitution solution that is discharged through the residual solution outlet 132 and includes a current measuring unit **142*a* and a voltage measuring unit 142*b***.

When the current measuring unit **142*a* and the voltage measuring unit 142*b* apply a D/C current and a D/C voltage to a microbe substitution solution, the electrical property calculation unit 140 can calculate electrical conductivity, but cannot calculate the permittivity. Accordingly, the current measuring unit 142*a* and the voltage measuring unit 142*b*** apply an A/C current and an A/C voltage to a microbe substitution solution.

Figure 6:
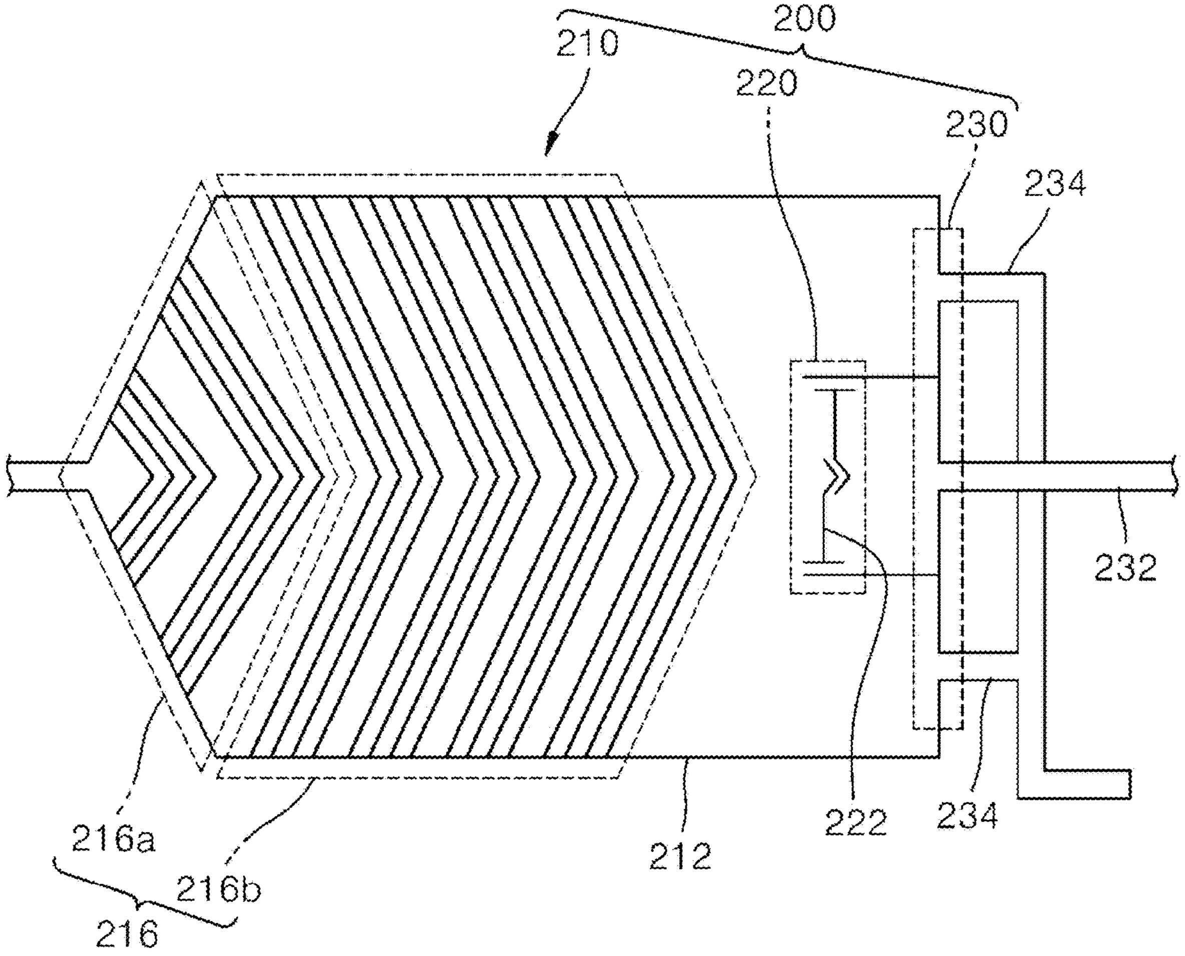
FIG. 6 is a cross-sectional view showing a microbe concentration measurement unit of the microbial concentration detection element according to an embodiment of the present disclosure.
Figure 7:
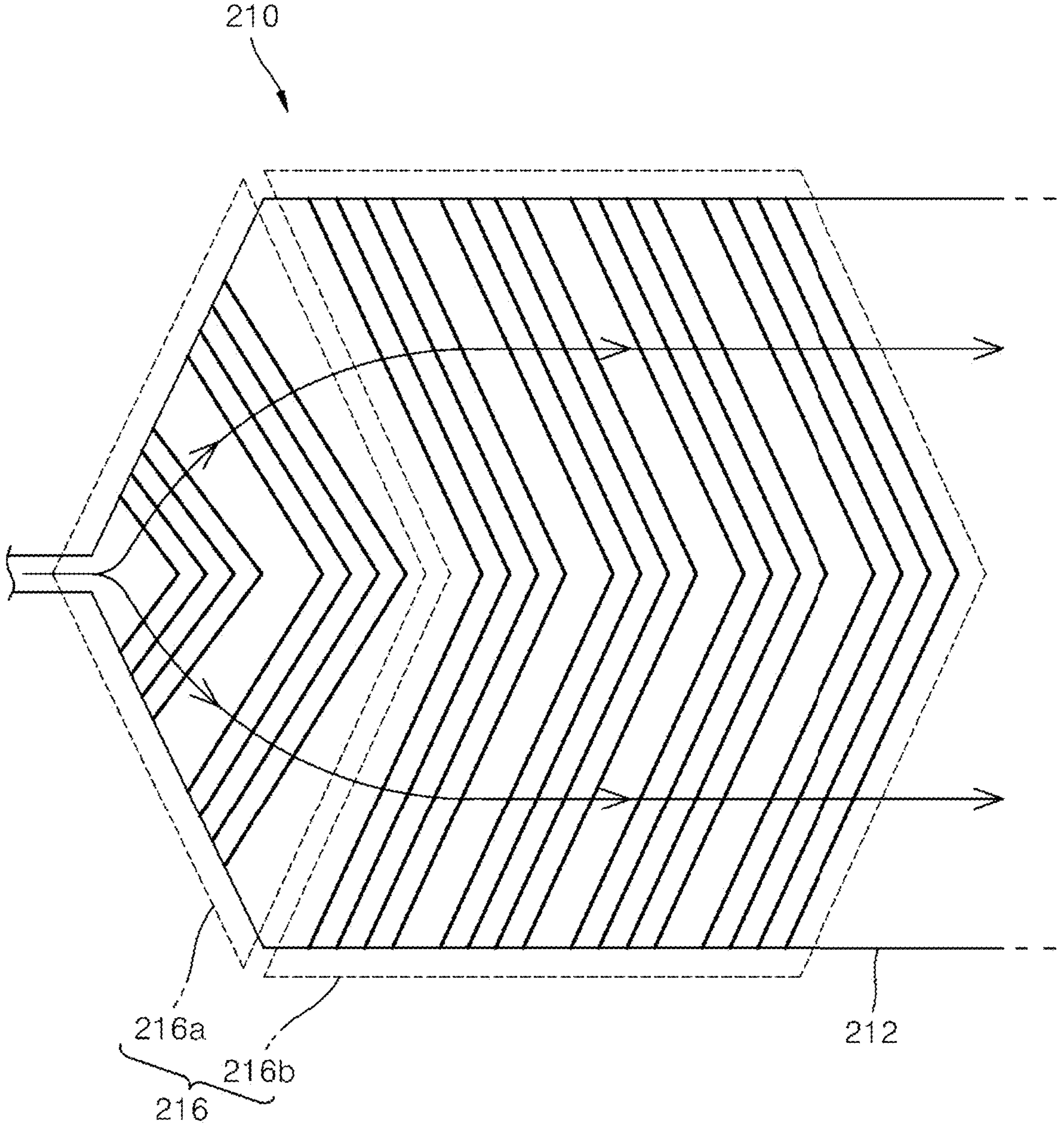
FIG. 7 is a cross-sectional view showing a microbe substitution solution reception part of the microbial concentration detection element according to an embodiment of the present disclosure.

Referring to FIGS. 6 and 7, the microbe concentration measurement unit 200 separates the microbe substitution solution into a microbe concentration solution and a filtered solution through dielectrophoresis on the basis of the electrical property information measured by the preprocessing unit 100, and then measures the microbial concentration of the microbe concentration solution.

The microbe concentration measurement unit 200 includes a separation part 210, a concentration measurement part 220, and a second discharge part 230.

The separation part 210 separates a microbe substitution solution into a microbe concentration solution and a filtered solution using positive dielectrophoresis force (DEP force).

The separation part 210 includes a substitution solution reception part 212, a herringbone electrode part 216, and a first power application part (not shown).

The microbe substitution solution discharged from the first discharge part 130 is received in the substitution solution reception part 212, and a plurality of herringbone electrode parts 216 is installed.

The herringbone electrode part 216 is formed in a herringbone pattern shape in which electrodes bend at predetermined angles and extend from bending points.

As the microbes contained in a microbe substitution solution in the substitution solution reception part 212 are moved along the bending points by positive dielectrophoresis force, the herringbone electrode part 216 separates the microbe substitution solution into a microbe concentration solution and a filtered solution. In detail, while a microbe substitution solution discharged from the substitution solution outlet 131 and flowing in the substitution solution reception part 212 moves toward the second discharge part 230, the herringbone electrode part 216 induces microbes contained in the microbe substitution solution to the bending points, whereby the microbe substitution solution is separated into a microbe concentration solution. Further, a filtered solution without the microbes induced to the bending points moves to the second discharge part 230.

The herringbone electrode part 216 includes a first electrode section 216*a* and a second electrode section 216*b*.

The first electrode section 216*a* is composed of a plurality of first electrodes arranged with predetermined gaps therebetween on the basis of flow of the microbe substitution solution, and the first electrodes are formed at different angles. When the microbe substitution solution flows into the substitution solution reception part 212, the first electrodes smoothly apply positive dielectrophoresis force even in curved flow of the microbe substitution solution due to a drag force generated in the microbe substitution solution, thereby inducting the microbes to the bending points.

The second electrode section 216*b* is composed of a plurality of second electrodes arranged with predetermined gaps therebetween on the basis of flow of the microbe substitution solution passing through the first electrode section 216*a*, and the second electrodes are formed at a uniform angle. The second electrodes smoothly apply positive dielectrophoresis force to straight flow of microbe substitution solution passing through the first electrode section 216*a*.

The first and second electrode sections 216*a* and 216*b* are sequentially arranged with a predetermined gap therebetween.

The first power application part applies power to the herringbone electrode part 216 on the basis of electrical property information calculated by the electrical property calculation unit 140. In detail, the first power application part applies an alternating current, which is suitable for separating a microbe concentration solution and a filtered solution, to the herringbone electrode part 216 on the basis of the CM factor, whereby an electric field is formed at the substitution solution reception part 212. Accordingly, positive dielectrophoresis force is generated in a microbe substitution solution through the herringbone electrode part 216.

The concentration measurement part 220 measures the microbe concentration of a microbe concentration solution separated by the separation part 210.

The concentration measurement part 220 includes a detection electrode part 222, a second power application part (not shown), and a microbe concentration detection part (not shown).

The detection electrode part 222 is installed in the substitution solution reception part 212 and captures microbes concentrated in a microbe substitution solution using positive dielectrophoresis force.

The detection electrode part 222 may include one or more pairs of IDE electrodes. However, the number of pairs of electrodes included in the detection electrode part 222 may be increased by a user to improve microbe detection sensitivity, depending on cases.

The second power application part applies power to the detection electrode part 222 for a predetermined time. In detail, the second power application part applies alternating current power to the detection electrode part 222 for a predetermined time, thereby preventing a loss of an intended function due to excessive capturing of microbes that are captured at the detection electrode part 222 when positive dielectrophoresis force is generated.

The microbe concentration detection part measures a total microbe concentration by measuring electrical signal variation generated for a predetermined time at the detection electrode part 222.

The second discharge part 230 includes a concentration solution outlet 232 and a filtered solution outlet 234.

A microbe concentration solution with microbes concentrated in the substitution solution reception part 212 is discharged through the concentration solution outlet 232 and a filtered solution produced by separation of microbes in the substitution solution reception part 212 is discharged through the filtered solution outlet 234.

Figure 8:
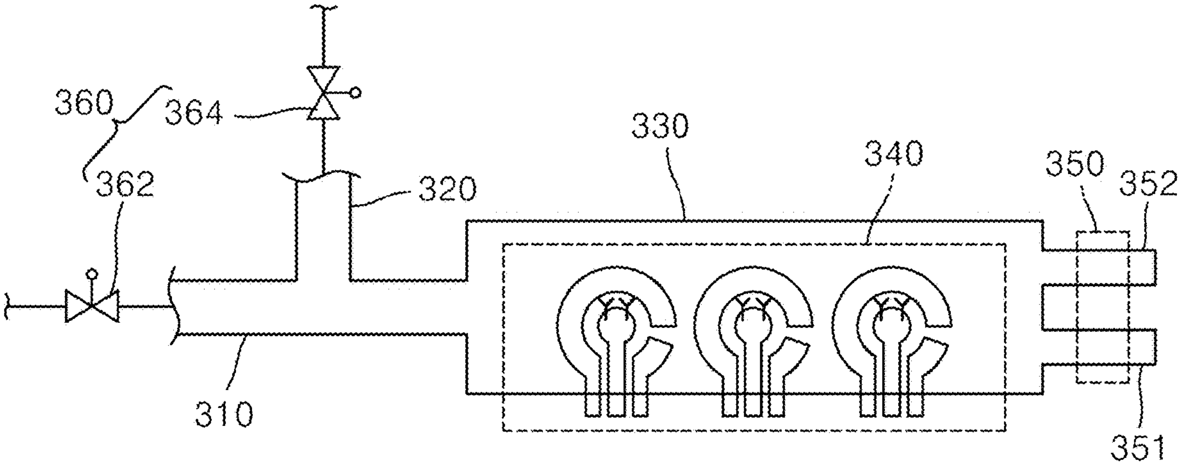
FIG. 8 is a cross-sectional view showing an electrochemical sensor unit of the microbial concentration detection element according to an embodiment of the present disclosure.

Referring to FIG. 8, the electrochemical sensor unit 300 includes a sample solution injection part 310, a reaction solution injection part 320, a solution reception part 330, an incubation part (not shown), a microbe strain-specific concentration measurement part 340, a solution discharge part 350, a shutoff valve 360, and a controller (not shown).

A microbe concentration solution discharged from the concentration solution outlet 232 is injected into the sample solution injection part 310.

The reaction solution injection part 320 is connected with the sample solution injection part 310 and a reaction solution is injected into the reaction solution injection part 320 for operation of the incubation part.

The solution reception part 330 is connected with the sample solution injection part 310, and the microbe concentration solution and the reaction solution are sequentially received in the solution reception part 330.

A plurality of incubation parts is installed in the solution reception part 330 and incubates microbes of a microbe concentration solution received in the solution reception part for a predetermined time. The incubation means a series of processes that combines a microbe (antigen) and an antibody to capture the microbe.

Different kinds of antibodies are fixed at the incubation parts, respectively, to be able to capture microbes by kinds.

The microbe strain-specific concentration measurement part 340 measures the concentration of the strain of each of microbes incubated in the incubation parts. In this configuration, the reaction solution is injected into the solution reception part to measure the concentration of the strain of each of microbes, and the microbe concentration solution is discharged.

The microbe strain-specific concentration measurement part 340 measures the concentration of the strain of each of microbes by measuring variation of an electrochemical signal that is generated in the reaction solution by combination of a microbe and an antibody (a current or voltage value that is generated by oxidation-reduction reaction.

The solution discharge part 350 is connected with the solution reception part, and the microbe concentration solution or the reaction solution is discharged through the solution discharge part 350.

The shutoff valve 360 blocks movement of a microbe concentration solution or a reaction solution. The shutoff valve 360 includes a first shutoff valve 362 installed at the sample solution injection part 310 and blocking movement of the microbe concentration solution and a second shutoff valve 364 installed at the reaction solution injection part 320 and blocking movement of the reaction solution.

The controller controls the first and second shutoff valves 362 and 364 such that the microbe concentration solution and a sample solution are sequentially received into the solution reception part 330. In detail, the controller shuts off the second shutoff valve 364, thereby allowing the microbe concentration solution to be injected into the solution reception part 330. Further, the controller shuts off the first shutoff valve 362, thereby allowing the reaction solution to be injected into the solution reception part 330.

Further, the controller may control general operation such that the microbe concentration solution and the reaction solution are injected or discharged, depending on cases.

In the microbial concentration detection element 10 in an unknown solution according to an embodiment of the present disclosure, the preprocessing unit 100, the microbe concentration measurement unit 200, and the electrochemical sensor unit 300 are connected to each other through a lumped parameter modeling, thereby maintaining each functions.

Further, in the microbial concentration detection element 10 in an unknown solution according to an embodiment of the present disclosure, hydraulic resistance values are designed in order of the electrochemical sensor unit 300, the microbe concentration measurement unit 200, and the preprocessing unit 100, thereby maintaining each function therebetween. In more detail, when the preprocessing unit 100, the microbe concentration measurement unit 200, and the electrochemical sensor unit 300 are connected to each other in this order, resistance values are changed and intended functions are lost, so resistance values are designed in order of the electrochemical sensor unit 300, the microbe concentration measurement unit 200, and the preprocessing unit 100.

An operation process of the microbial concentration detection element 10 in an unknown solution according to an embodiment of the present disclosure described above is as follows.

When an unknown solution and a reference solution are fed into the inlet part 110, microbes contained in the unknown solution fed through the inlet part 110 are transferred into the reference solution by acoustophoresis at the substitution part 120, whereby a microbe substitution solution is produced. In this process, the microbe substitution solution is discharged through the first discharge part 130, and simultaneously, the electrical property calculation unit 140 calculates electrical property information of the microbe substitution solution.

Next, the microbe substitution solution discharged from the first discharge part 130 is received into the substitution solution reception part 212. Further, drag force is generated by flow of the microbe substitution solution.

Further, the first power application part applies power based on the electrical property information to the herringbone electrode part 216, whereby positive dielectrophoresis force is generated at the substitution solution reception part 212.

Accordingly, the microbes are moved along the bending points of the herringbone electrode part 216 by the positive dielectrophoresis force, whereby the microbe substitution solution is separated into a microbe concentration solution. Further, microbe substitution solution is moved toward the second discharge part 230 due to drag force, whereby it is separated into a filtered solution. Simultaneously, the microbe concentration detection part measures electrical signal variation generated by applying power to the microbe substitution solution for a predetermined time, whereby it is possible to find out the microbial concentration.

Meanwhile, in order to find out the concentration of the strain of each of microbes, the controller shuts off the second shutoff valve 364 and the microbe concentration solution is injected into the solution reception part 330 through the sample solution injection part 310. Next, the incubation parts start to incubate the microbes in the microbe concentration solution.

When the incubation parts finish incubation of the microbes for a predetermined time, the controller shuts off the first shutoff valve 362 and the reaction solution is injected into the solution reception part 330 through the reaction solution injection part 320. Simultaneously, the microbe concentration solution received in the solution reception part 330 is discharged to the solution discharge part 350.

Next, the microbe strain-specific concentration measurement part 340 measures electrical signal variation such as a current or voltage value generated by oxidation-reduction reaction of the reaction solution, whereby it is possible to find out the concentration of the strain of each of captured microbes.

Therefore, the microbial concentration detection element 10 in an unknown solution according to an embodiment of the present disclosure supplies power to the herringbone electrode part 216 on the basis of electrical property information of the preprocessed microbe substitution solution, thereby being able to separate the microbe substitution solution into a microbe concentration solution and a filtered solution through positive dielectrophoresis force.

Further, according to the microbial concentration detection element 10 in an unknown solution of an embodiment of the present disclosure, the a herringbone electrode part 216 is designed on the basis of flow of a microbe substitution solution flowing into the substitution solution reception part 212, whereby it is possible to smoothly apply positive dielectrophoresis force to microbes.

The description of the proposed embodiments is provided to enable those skilled in the art to use or achieve the present disclosure. Various modifications of the embodiments would be apparent to those skilled in the art, and general principles defined herein may be applied to other embodiments without departing from the scope of the present disclosure. Therefore, the present disclosure is not limited to the embodiments proposed herein and should be construed in the widest range that is consistent with the principles proposed herein and new characteristics.

The invention claimed is:

1. A microbial concentration detection element in an unknown solution, comprising:
- a preprocessing unit configured to produce a microbe substitution solution by transferring microbes in an unknown solution containing detection target microbes into a reference solution through acoustophoresis, and to calculate electrical property information of the microbe substitution solution; and
- a microbe concentration measurement unit configured to separate the microbe substitution solution into a microbe concentration solution and a filtered solution through dielectrophoresis on the basis of the electrical property information measured by the preprocessing unit, and then measure a microbial concentration of the microbe concentration solution.

2. The microbial concentration detection element of claim 1, wherein the preprocessing unit includes:
- an inlet part into which the unknown solution and the reference solution are separated fed;
- a substitution part configured to produce a microbe substitution solution by transferring microbes contained in the unknown solution fed through the inlet part into the reference solution through acoustophoresis;
- a first discharge part configured to separately discharge the microbe substitution solution produced at the substitution part and the unknown solution; and an electrical property calculation unit configured to calculates electrical property information of the microbe substitution solution that is discharged through the first discharge part.

3. The microbial concentration detection element of claim 2, wherein the electrical property calculation unit includes:

an impedance measuring unit configured to measure impedance of the microbe substitution solution that is discharged through the first discharge part; and a calculator configured to calculate electrical property information on the basis of impedance measured by the impedance measuring unit.

4. The microbial concentration detection element of claim 3, wherein the impedance measuring unit includes:

a current measuring unit configured to measure a current that is applied to the microbe substitution solution that is discharged through the first discharge part; and a voltage measuring unit configured to measure a voltage that is applied to the microbe substitution solution that is discharged through the first discharge part.

5. The microbial concentration detection element of claim 3, wherein the electrical property information is electrical conductivity, permittivity, and a Clausius-Mossotti (CM) factor.

6. The microbial concentration detection element of claim 5, wherein the microbe concentration measurement unit includes:

a separation part configured to separate the microbe substitution solution into a microbe concentration solution and a filtered solution using positive dielectrophoresis force;

a concentration measurement part configured to measure a microbe concentration of the microbe concentration solution separated by the separation part; and a second discharge part configured to separately discharge the microbe concentration solution and the filtered solution separated by the separation part.

7. The microbial concentration detection element of claim 6, wherein the separation part includes:

a substitution solution reception part configured to receive the microbe substitution solution;

a plurality of herringbone electrode parts installed at the substitution solution reception part, formed in a herringbone pattern shape in which electrodes bend at predetermined angles and extend from bending points, and configured to separate the microbe substitution solution into a microbe concentration solution and a filtered solution as microbes contained in the microbe substitution solution in the substitution solution reception part are moved along the bending points by positive dielectrophoresis force; and a first power application part configured to apply power to the herringbone electrode part on the basis of electrical property information calculated by the electrical property calculation unit so that positive dielectrophoresis force can be generated at the herringbone electrode part.

8. The microbial concentration detection element of claim 7, wherein the herringbone electrode part includes a first electrode section and a second electrode section, the first and second electrode sections are sequentially arranged with a predetermined gap therebetween, the first electrode section is composed of a plurality of first electrodes arranged with predetermined gaps therebetween on the basis of flow of the microbe substitution solution such that the microbes can be induced to the bending points by smoothly applying positive dielectrophoresis force to microbes contained in the microbe substitution solution received in the substitution solution reception part, the second electrode section is composed of a plurality of second electrodes arranged with predetermined gaps therebetween on the basis of flow of the microbe substitution solution passing through the first electrode section such that positive dielectrophoresis force can be smoothly applied, the first electrodes are formed at different angles, and the second electrodes are formed at a uniform angle.

9. The microbial concentration detection element of claim 7, wherein the concentration measurement part includes:

a detection electrode part installed in the substitution solution reception part and configured to capture microbes concentrated in a microbe substitution solution using positive dielectrophoresis force;

a second power application part configured to apply power to the detection electrode part for a predetermined time so that positive dielectrophoresis force can be generated; and a microbe concentration detection part configured to measure a total microbe concentration by measuring electrical signal variation generated for a predetermined time at the detection electrode part.

10. The microbial concentration detection element of claim 9, wherein the detection electrode part is composed of one or more pairs of IDE electrodes.

11. The microbial concentration detection element of claim 1, further comprising an electrochemical sensor unit configured to measure a concentration of a strain of each of microbes in a microbe concentration solution that is discharged from the microbe concentration measurement unit, wherein the electrochemical sensor unit includes:

a sample solution injection part into which the microbe concentration solution is injected;

a reaction solution injection part that is connected with the sample solution injection part and into which reaction solution is injected;

a solution reception part that is connected with the sample solution injection part and into which the microbe concentration solution and the reaction solution are sequentially received;

an incubation part configured to incubate microbes of the microbe concentration solution received in the solution reception part for a predetermined time;

a microbe strain-specific concentration measurement part configured to measure a concentration of a strain of each of microbes incubated in the incubation part; and a solution discharge part connected with the solution reception part and configured to discharge the microbe concentration solution or the reaction solution from the solution reception part.

12. The microbial concentration detection element of claim 11, comprising:

a shutoff valve installed at the sample solution injection part and configured to block movement of the microbe concentration solution or the reaction solution; and a controller configured to control the shutoff valve such that a microbe concentration solution and a filtered solution are sequentially received in the solution reception part in order to measure a concentration of a strain of each of microbes incubated in the incubation part.

* * * * *